United States Patent [19]

Girot et al.

[11] Patent Number: 4,478,713
[45] Date of Patent: Oct. 23, 1984

[54] AUTOMATIC INSTALLATION FOR LIQUID CHROMATOGRAPHY

[75] Inventors: Pierre Girot, Paris; Egisto Boschetti, Chatou, both of France

[73] Assignee: Pharmuka Laboratoires, Gennevillers, France

[21] Appl. No.: 535,308

[22] Filed: Sep. 23, 1983

[51] Int. Cl.³ .............................................. B01D 15/08
[52] U.S. Cl. ................................... 210/101; 210/104; 210/142; 210/198.2
[58] Field of Search .............. 210/101, 104, 142, 198.2

[56] References Cited

U.S. PATENT DOCUMENTS

| | | | |
|---|---|---|---|
| 2,692,820 | 10/1954 | Alway | 210/198.1 |
| 3,012,156 | 12/1961 | Simmons | 210/142 |
| 3,701,609 | 10/1972 | Bailey | 210/198.2 |
| 3,826,905 | 8/1976 | Valkama | 127/46.1 |
| 3,963,614 | 6/1976 | Ozowa | 210/198.2 |
| 4,116,046 | 9/1978 | Stein | 210/198.2 |
| 4,151,086 | 4/1979 | Frosch | 210/142 |
| 4,311,586 | 1/1982 | Baldwin et al. | 210/198.2 |
| 4,422,942 | 12/1983 | Allington | 210/101 |

FOREIGN PATENT DOCUMENTS

3030069 3/1982 Fed. Rep. of Germany .
2388585 11/1978 France .

OTHER PUBLICATIONS

Fresenius' Zeitschrift fur Analytische Chemie, vol. 261, fascicule 4/5, 1972.
International Laboratory, vol. 9, No. 11/12, (1979).
Measurement Techniques, vol. 17, No. 11, Nov. 1974.

*Primary Examiner*—John Adee
*Attorney, Agent, or Firm*—Scully, Scott, Murphy and Presser

[57] ABSTRACT

In the automatic installation for liquid chromatography according to the invention, the container of product to be fractionated is associated to a measuring container and is provided, as are the containers of eluents, with low level detector means; feed valves are interposed between said containers and the injection pump whereas output valves are interposed between the outlet from the column and the collector containers; a control unit comprises a safety device connected to the low level detectors to control the stoppage of the pump whenever necessary, and a control device receiving the signals from detection means connected to the output of the column and controlling the measuring container and said valves to perform successive cycles of chromatography each one including the steps of injecting a quantity of product, admitting at least one eluent and collecting the or each corresponding fraction.

12 Claims, 9 Drawing Figures

AUTOMATIC INSTALLATION FOR LIQUID CHROMATOGRAPHY

The present invention relates to an automatic installation for liquid chromatography, of the type comprising a chromatographic column, a container of the product to be fractionated, and at least one container of eluent, said containers being connectable with the top of the column via an injection pump, detection means connected to the output of the column and supplying at least one measuring signal representing a characteristic of the liquid discharged from the bottom of the column, means for collecting fractions with at least one collector container which is connectable with the base of the column via an automatically-controlled output valve, and a control unit receiving the measuring signal and comprising means for controlling the fractions collecting means.

Chromatography is a method for separating the constituents of a mixture, which method can be used for either analytical or industrial purposes The field of application of the invention is more particularly but not exclusively that of industrial chromatography.

In this case, the object is a technique of production by extraction of one or more known products from the mixture containing them. By way of indication, industrial chromatography can be used for separating proteins, such as for extracting albumin from blood plasma. It is normal in this case to use columns having a volume of several scores liters, and even of several hundreds liters. Such installations have no common measures with the apparatus used in analytical chromatography; moreover, whereas the object of analytical chromatography is to separate the often very numerous constituents of a mixture with a view to identifying them and to measuring their proportion in the mixture, industrial chromatography is designed to extract a restricted number of products from a mixture which is known to contain them.

In industrial chromatography, the preparation of the columns requires minute care and takes extremely long time. Moreover, the products involved can be extremely expensive—this is particularly the case with blood plasma. For these reasons, the installations require constant monitoring, and this up to now has been carried out by qualified staff in order to prevent any incidents liable to cause a degradation of the column or a loss of product It is therefore desirable to mechanize these installations in order to lower production costs.

Different automatic systems have already been proposed in the field of chromatography.

For example, it is known to use means giving an automatic reading of a chromatogram in order to determine in particular the fraction quantity corresponding to each peak.

It is also known to collect automatically the different fractions by comparing the measuring signal produced by the detection means with a given threshold, in order to connect the column with a collector container when the measuring signal goes beyond said threshold, and to bring another collector container in the collecting position for collecting the next fraction. The collector containers are placed on a conveyor means, such as for example a rotary platform, moving stepwise.

These automatic systems are only concerned with one part of the overall process. Thereafter research was centered on finding a more advanced automation, and it was proposed to this effect to use a preprogrammed clock producing different control signals at predetermined time intervals so as to create a cycle of chromatography. The times at which different operations—such as injection of the product to be fractionated, admission of the eluent, collection of a fraction—are due to be performed are preset from a sample. It is therefore understandable that the results thus obtained can only be satisfactory if the operational conditions are exactly the same as with the sample. But this is practically never so due to the fact that parameters such as loss of load in the column are not controllable and are subject to variations.

It is the object of the present invention to propose a fully-automated liquid chromatography installation, capable of producing successive cycles of chromatography without the results being affected by variations in operation parameters such as the flow of liquid inside the column.

It is also the object of the invention to provide a liquid chromatography installation which only requires superficial monitoring by an operator, without any risk of the column deteriorating or of losing any of the product.

These objects are reached with an installation of the type defined at the beginning of the description, and wherein, according to the invention:

a level detector is provided for each container of product to be fractionated and of eluent, which detector produces a low level signal whenever the level of the liquid inside the container is below a predetermined threshold, automatically controlled feed valves are mounted between the injection pump and each container of product to be fractionated and eluent, respectively, a measuring device is provided for the container of the liquid to be fractionated, to allow injection into the column of a pre-determined quantity of said product, and the control unit comprises: a control device receiving the or each measuring signal produced by the detection means and controlling on the one hand, the feed and output valves and, on the other hand, the measuring device, to produce successive cycles of chromatography each one including at least the consecutive operations of injecting into the column a set quantity of the product to be fractionated, of admitting in the eluent, and of collecting a fraction; and a safety device connected to the level detectors to control the stoppage of the pump and prevent admission of product to be fractionated or of eluent into the column when the corresponding level detector produces a low-level signal.

Thus, the different operations performed through one cycle are not controlled at preset time intervals, on the contrary, they are carried out at times which are determined in relation to the information supplied by the detection means. Also, due to the use of the measuring device it is possible to automatically perform successive cycles without the operator intervening otherwise than periodically necessary to fill the containers with the product to be fractionated and with eluent, and to empty the collector or collectors. Moreover, the safety device prevents the accidental injection of air, which would put the column out-of-order.

Preferably, the detection device comprises a plurality of detectors producing different measuring signals representing different characteristics of the liquid discharged from the column.

The control device comprises in manner known per se, a comparator to initiate the collection of one fraction when a measuring signal produced by the detection means crosses, in one direction, a first preset and adjustable threshold. Advantageously, the control device comprises a second comparator to interrupt the collection of the fraction when the measuring signal crosses in the other direction a second preset threshold adjustable independently of the first. Compared with the known collecting systems wherein one and the same threshold is used to initiate and interrupt the collection of a fraction, the present two independent thresholds system enables to freely adjust the fraction of one "peak" of the measuring signal during which the collection is taking place. This is a particular advantage knowing that, in some cases, it is desirable to limit the collection of a fraction to one part of the peak, for example to avoid collecting interfering products in addition to the required product.

Advantageously, the control device further comprises means for controlling the admission of an eluent into the column and means of detecting the balancing of the column with the admitted eluent, said means responding to at least one measuring signal to control the injection of a quantity of product to be fractionated. Said balance detection means comprise a comparison device receiving said measuring signal and producing an output signal when the amplitude of the measuring signal is within an adjustable predetermined range. The measuring signal used can for example represent the pH and/or the concentration of the liquid discharged from the column.

The separate recovery of several different fractions on one and the same column is achieved, after injection of the product to be fractionated, by successively allowing the flow of several eluents whose elution powers increase gradually. Then according to another special feature of the installation of the invention said installation comprises a plurality of containers of eluent and the control device receives the measuring signal or signals from the detection device for controlling the successive cycles, each one comprising: the injection of a predetermined quantity of product to be fractionated, the admission of a first eluent into the column, the collection of a first fraction, the admission of a second eluent into the column, the collection of a second fraction, and if necessary, at least one additional sub-cycle comprising the admission of another eluent into the column and the collection of the corresponding fraction, and finally the admission of the first eluent into the column to re-balance it before the start of the next cycle.

The admission of eluent is for example controlled in response to the end of the injection of the product to be fractionated or to the end of the collection of one fraction.

The different fractions are collected in different collector containers. Said containers could be placed on a conveyor device bringing them successively in collecting position, a single output valve being provided to connect the column with the different collectors. However, in the case of installations used for industrial chromatography, the volumes treated are relatively high and it is then preferable to use several fixed collectors, their number being at least equal to the number of fractions to be collected. Each collector can be connected with the column either by means of a joint output valve with interposition of a distributor device, i.e. by means of a special output valve controlled by said control device. Advantageously, a level detector is provided for each collector, in order to produce a high level signal when the level of the liquid inside the collector rises above a predetermined threshold, said detector being connected to the safety device to prevent collection of said liquid when a high level signal is present.

Thus, the process is stopped when a container of product to be fractionated or of eluent becomes empty or when a collector container risks to overflow. The level signals can thus be used to actuate a warning device indicating to the operator that a container needs to be filled or emptied.

The invention will be more readily understood on reading the following description with reference to the accompanying drawings, in which.

Figure 1:
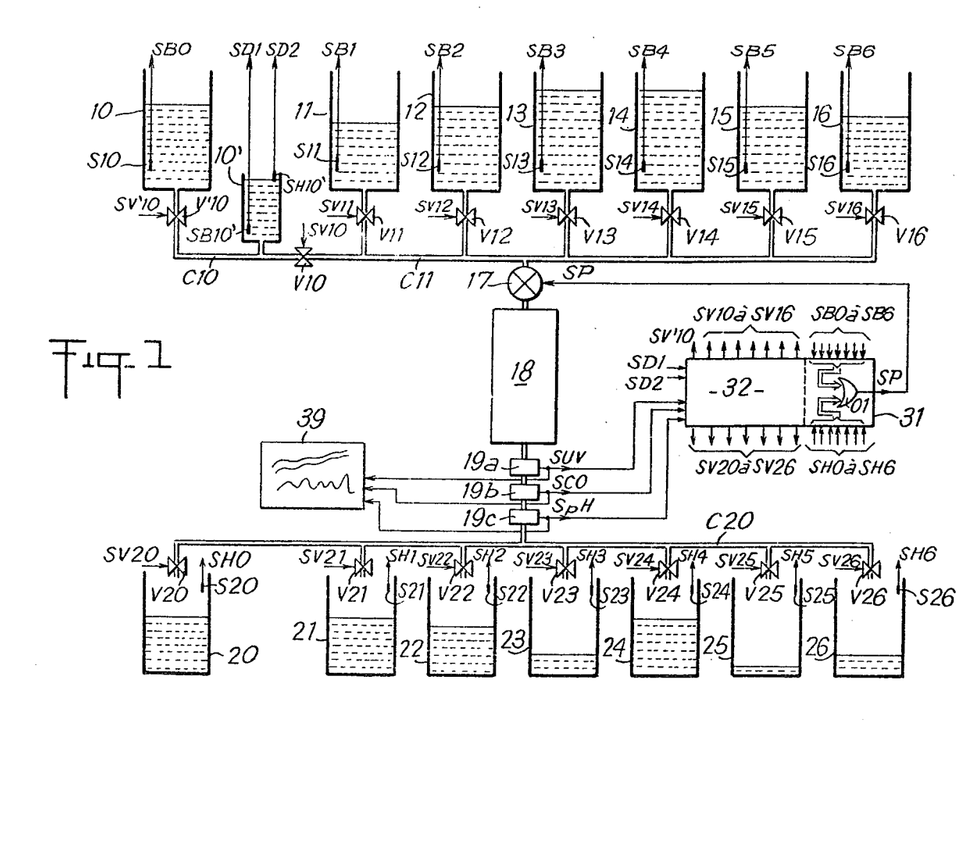
FIG. 1 is a general diagram of one embodiment of a chromatography installation according to the invention.

Referring first to FIG. 1, this shows an installation comprising a container 10 of product to be fractionated, which container is equipped with a measuring bottle 10', and a plurality of containers of eluent 11 to 16. An electrovalve V'10 is mounted on a conduit C10 connecting the container 10 with the measuring bottle 10'. Said latter and the containers or eluent can communicate with a chromatographic column 18 via a conduit C11 and an injection pump 17. Between conduit C11 and the measuring bottle 10' and each one of containers 11 to 16, are interposed electrovalves V10 to V16 respectively. Detection means consisting of a plurality of detectors 19a, 19b, 19c are provided at the outlet from the column. Downstream of these detectors, the column 18 is connected to conduit C20. Collector 20 to 26 can communicate with conduit C20 via electrovalves V20 to V26 respectively. Collector 20 is designed to collect the rejected part whereas containers 21 to 26 are designed to collect the eluents containing the recoverable products. Each one of containers 10 to 16 is provided with a level probe, S10 to S16 respectively, designed to produce a signal (SB0 to SB6) when the level of the liquid inside the container goes below a predetermined minimum threshold corresponding to the position of the probe inside the container. Similar probes S20 to S26 are placed in containers 20 to 26, but these are designed to produce a signal (SH0 to SH6) when the level of the liquid inside said container rises above a predetermined maximum threshold. Two other probes SB10' and SH10' are placed inside the measuring container 10 at different heights, the difference of level between the lower probe SB10' and the higher probe SH10' defining the volume of a quantity of product to be fractionated.

A control unit 30 comprises a safety device 31 receiving signals SB0 to SB6 from probes S10 to S16, and signals SH0 to SH6 from probles S20 to S26 and sending a signal SP to the pump 17 to stop the operation of the latter in order to prevent draining off from one of containers 10 to 16 whenever, in said container, the minimum level threshold has been reached, and to prevent one of containers 20 to 26, from filling up, whenever, in said container, the maximum level threshold has been exceeded. Signals SB0 and SB6 and SH0 to SH6 are received via an OR-type gate 01 which delivers signal SP on its output. A pressure sensor can be provided between the pump 17 and the top of the column 18 to produce a signal on an input of the gate 01 in order to control the stoppage of the pump in case of an abnormal excess of pressure. The unit 30 further comprises a control device 32 which receives the signals SD1 and SD2 produced by the probes SB10' and SH10' as well as measuring signals SUV, SCO and spH supplied by detectors 19a, 19b and 19c and representative of the different characteristics of the liquid discharged from the column. In response to the received signals, the device 32 controls electrovalves V'10, V10 to V16 and V20 to V26 via respective signals SV'10, SV10 to SV16 and SV20 to SV26.

Finally, signals SUV, SCO and SpH are also transmitted to a multi-way graph recorder 39.

In conventional industrial liquid chromatography, the process is as follows. Before the start of a cycle, i.e. before injecting a quantity of product to be fractionated, the column is balanced with the first eluent. To this effect, the first eluent is caused to flow into the column until the liquid discharged from said column has substantially the same characteristics as the first eluent, for example, the same pH and/or a similar ion strength. The columns having been thus balanced, the admission of the first eluent is stopped and a quantity of the product to be fractionated is injected. Then, different eluents are caused to flow successively, the corresponding fraction being collected each time. The eluents are solutions whose chemical composition can be either identical or different, with concentration and pH rates which may be different. The admission of eluents is mostly achieved according to increasing concentration order, the elution power in these cases being higher as the concentration increases, whereas such a rule is not true for the pH. For every eluent, a measuring signal produced by a detector and representing a characteristic of the liquid discharged from the column is monitored and the corresponding fraction is collected throughout all or part of a peak of the measuring signal. When the last fraction has been collected, the first eluent is once again admitted into the column for a re-balancing of the latter before the next cycle.

The installation illustrated in FIG. 1 enables automatic performance of the operations indicated hereinabove. In the illustrated example, six containers of eluent 11 to 16 and six corresponding collectors of fractions (21 to 26) are provided. But obviously the installation can comprise more or less than six such containers and collectors, depending on the requirements. And, as explained hereinafter, it is possible to envisage a simple pre-setting of the control unit, to work the installation with any number of eluents.

Detectors 19a, 19b, 19c supply to the control device the information necessary to detect the balance of the column and the peaks. Preferably, a number of detectors of different types are used. One or more such detectors can be given to detecting the balance of the column whereas the peaks are detected from the signal of at least one other detector. To detect the peaks, any detector of a known type can be used, depending in particular on the nature of the fractions to be collected, for example a U.V. detector 19a. To detect the balance of the column, it is possible to use a pH tester or an ion-detector. In the illustrated example, both an ion-detector 19b (or concentration detector) and a pH detector 19c are used. The pH detector 19c is a pH probe of conventionally known type. To detect the concentration, it is known to use a conductimeter dipped into the liquid and producing a signal representing the electrical conductivity of the liquid. However, to prevent any phenomenon of electrolysis related to the passage of current through a liquid, the concentration detector 19b can be of the type illustrated in FIG. 2.

Figure 2:
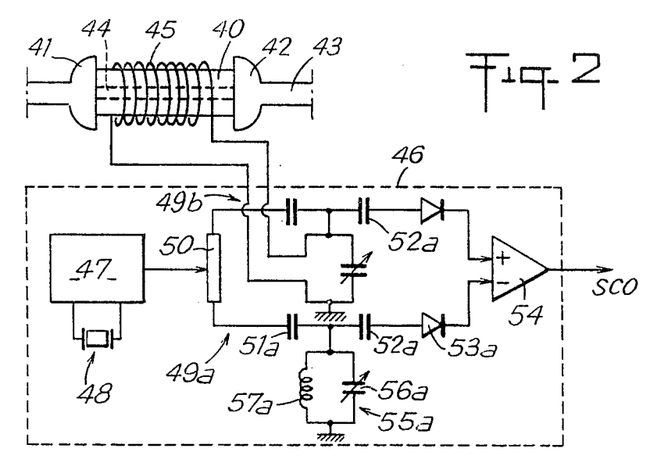
FIG. 2 is a diagram of one embodiment of the concentration detector of the installation shown in FIG. 1.

Said detector comprises a tube 40 in insulating material, such as glass, intercalated by means of connectors 41, 42 on a pipe 43, shunt-connected to the output pipe of the column. The liquid whose ion-concentration is to be measured flows through the passage 44 made in the center of tube 40. The diameter of said passage 44 is relatively small (between 1 and 2 mm for example). A coil 45 winds around the tube 40, a variation in the concentration of the liquid inside the tube causing a corresponding variation of the coil inductance. Said coil is connected to a circuit 46 which produces the signal SCO representative of the inductance of the coil 45. Said circuit 46 comprises an oscillator 47 stabilized by a quartz 48 and producing a high frequency signal applied symmetrically to two branches 49a, 49b via a resistive divider 50. Branch 49a comprises, in series, two capacitors 51a, 52a, and a diode 53a between the divider 50 and an input of a differential amplifier 54. A resonant circuit 55a composed of a capacitor 56a adjustable in parallel on a coil 57a is connected between the point common to the two capacitors 51a, 52a and the earth. Branch 49b is connected between the divider 50 and the other input of amplifier 54 and its structure is identical to that of the branch 49a, the coil of the resonant circuit being constituted by the coil 45. Any unbalance between branches 49a and 49b is an indication of the value of the ion-concentration in the liquid flowing through the tube 40 and is converted into a signal SCO outputted by amplifier 54. The resonant circuits are tuned to a frequency which is slightly different from that of the signal produced by oscillator 47, the adjustment being such that the range of the concentrations to be measured corresponds to a substantially linear part of the down (or up) portion of the resonance curve.

Control device 32 is now being described in greater detail with reference to FIGS. 3 to 9.

Figure 3:
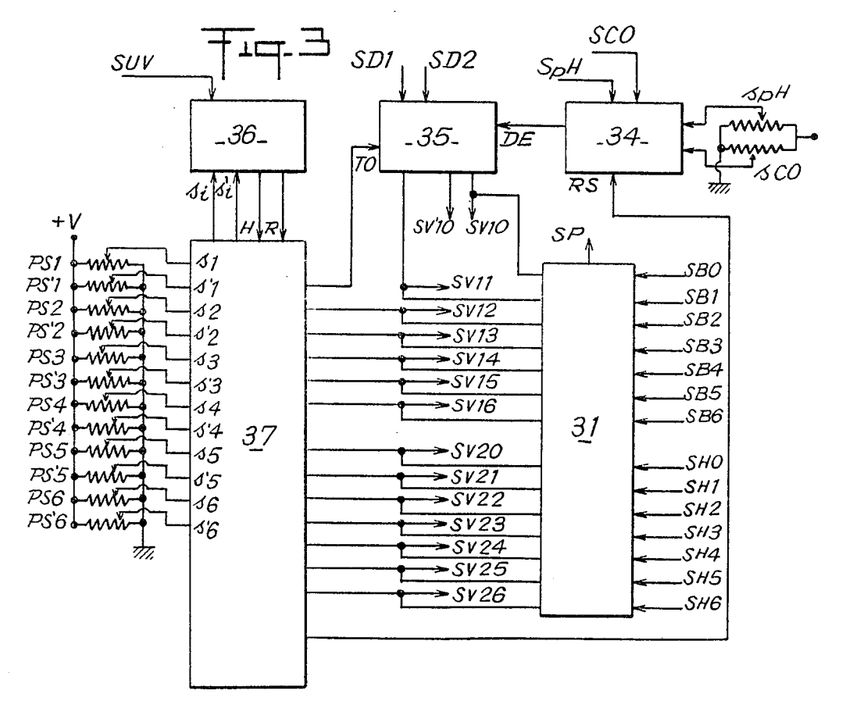
FIG. 3 is a general diagram of an embodiment of the control unit of the installation according to FIG. 1, FIGS. 4 to 7 are special diagrams of different circuits of the control unit shown in FIG. 3.

Said control device essentially comprises a detection circuit 34 detecting the balance of the column 18, a circuit 35 controlling the injection of a quantity of product to be fractionated, a fraction collection control circuit 36 and a switching circuit 37.

Circuit 34 (FIG. 4) comprises a circuit 34a receiving the measuring signal SpH and a reference signal spH supplied by a fader PpH, and a circuit 34b receiving the measuring signal SCO and a reference signal sCO supplied by a fader PC0.

Figure 4:
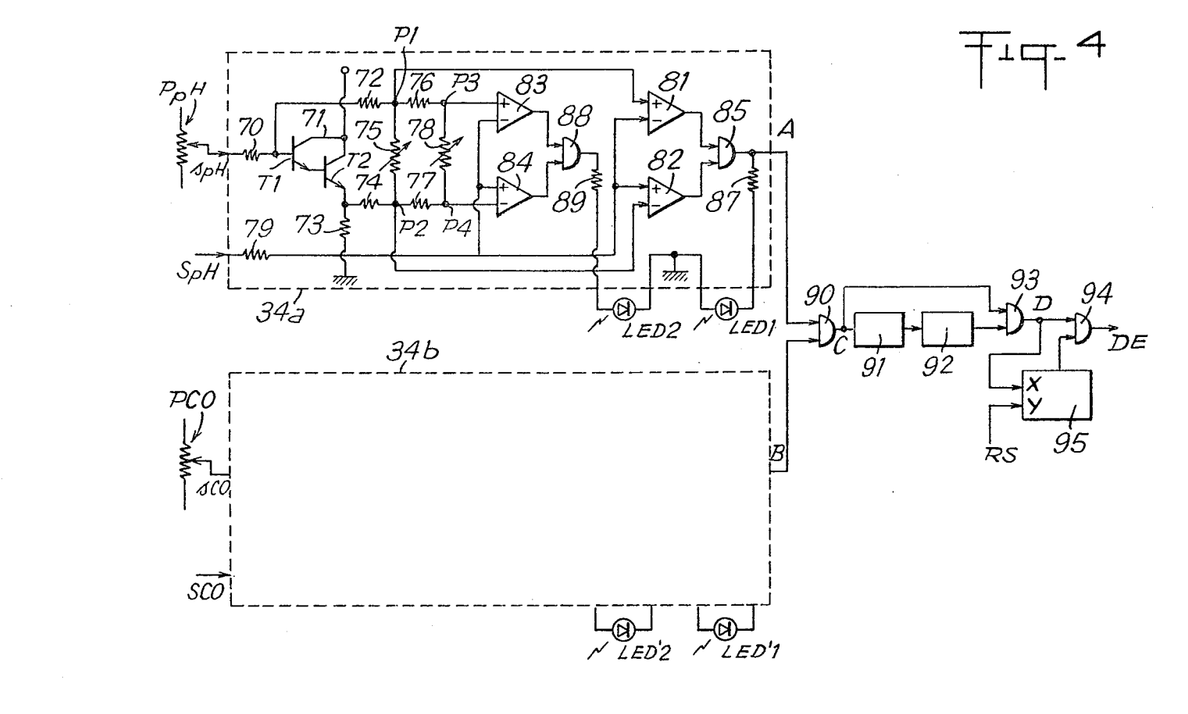

In circuit 34a, the signal spH is applied by a resistor 70, on the one hand to the input of a Darlington circuit 71 with two transistors T1, T2 and on the other hand to a node P1 via a resistor 72. In output of the Darlington circuit 71, the transmitter-collector path of transistor T2 is in series with a resistor 73 between a terminal of potential +V and the earth, whereas transmitter of T2 is connected to a node P2 via resistor 74. An adjustable resistor 75 is connected between P1 and P2. Owing to this particular connection, there is between the nodes P1 and P2 a potential difference ΔpH of constant amplitude whatever the potential of point P1 or P2. Potentiometer PpH enables to adjust this potential and thus to move inside a given setting range a potential "window" of given width ΔpH, said width being itself adjustable by acting on adjustable resistor 75. Points P1 and P2 are connected via respective resistors 76, 77 to two points P3, P4 between which is connected an adjustable resistor 78. Resistors 76, 77 and 78 form a voltage divider permitting to define between points P3 and P4 a second window of potential ΔpH', contained inside the first. The width of said second window is smaller than the width of the first and can be adjusted by resistor 78. Moreover, by selecting equal values for the resistors 76 and 77, the second window is situated in the center of the first. Points P1 and P3 are connected respectively to the non-reversing inputs of two amplifiers 81, 83 whereas points P2 and P4 are connected respectively to the reversing inputs of two amplifiers 82, 84. The signal SpH is applied via a resistor 79, to the reversing inputs of amplifiers 81, 83 and to the non-reversing inputs of amplifiers 82, 84. The outputs of amplifiers 81 and 82 are connected to the inputs of an AND type gate 85, and an electroluminescent diode LED1 is connected in series with a resistor 87 between the earth and the output of gate 85. Finally, the output of amplifiers 83 and 84 are connected to the inputs of an AND-type gate 88, whose output is connected to the earth via a resistor 89 and another electroluminescent diode LED2.

The aforedescribed circuit 34a works as follows. When the amplitude of the signal SpH is within the first window ΔpH, i.e. when this amplitude is between the values pH1 and pH2 of the potentials of points P1 and P2, the outputs of amplifiers 81, 82 working as comparators, are both at a high logic level. In this case only, there is a signal A of high logic level outputted from gate 85 and the diode LED1 lights up. When the amplitude of the signal SpH is not only contained in the first window, but also in the second window ΔpH', a signal A' of high logic level is outputted from gate 88 and the diode LED2 lights up. The presetting of circuit 34a is achieved by introducing directly into the pH detector 19c a flow of the eluent with which the column is subsequently to be balanced, and by adjusting the potentiometer PpH until diode LED2 lights up. The pH reference value then corresponds substantially to the middle of the window ΔpH. Thereafter, to detect the balancing of the column, only signal A is used, which signal indicates that the pH is between the limits pH1 and pH2, inside window ΔpH.

Circuit 34b is identical in structure and operation to circuit 34a. An electroluminescent diode LED'2 is used for pre-setting this circuit by means of potentiometer PC0 when the eluent flows directly through the concentration detector 19b. Thereafter, when the column is being balanced, a signal B is produced and a diode LED'1 lights up when the concentration is between the limits CO1 and CO2 inside the preset window ΔCO.

An AND-type gate 90 receives signals A and B and supplies a signal C when the measured pH and concentration are within the preset limits. To avoid untimely detection, due for example, to the passage of an air bubble, said signal C is not registered directly, but releases a monostable circuit 91, which in turn releases a second monostable circuit 92. Circuit 91 generates a relatively long pulse, lasting for example one minute. This is long compared to the transient phenomenon represented by the passage of an air bubble, but it is short compared to the duration of the phases of a chromatographic cycle. Circuit 92 generates a much shorter pulse. The outputs of gate 90 and of monostable 92 are connected to the inputs of an AND-type gate 93. The output signal of gate 93 is applied to the input of an AND-type gate 94 and to the input X of a flip-flop 95. In response to the signal D outputted from gate 93, an output terminal of flip-flop 95 passes to the low logic level, this blocking the gate 94. Thus, as soon as signal C is issued, monostable 91 is released and if signal C is still present at the end of the pulse delivered by said monostable, signal D is delivered and a balance detection pulse DE is outputted from gate 94. Signal D also releases flip-flop 95, this preventing the registering of any subsequent signal D until flip-flop 95 is reset by a signal RS applied to an input Y of said flip-flop 95.

Figure 5:
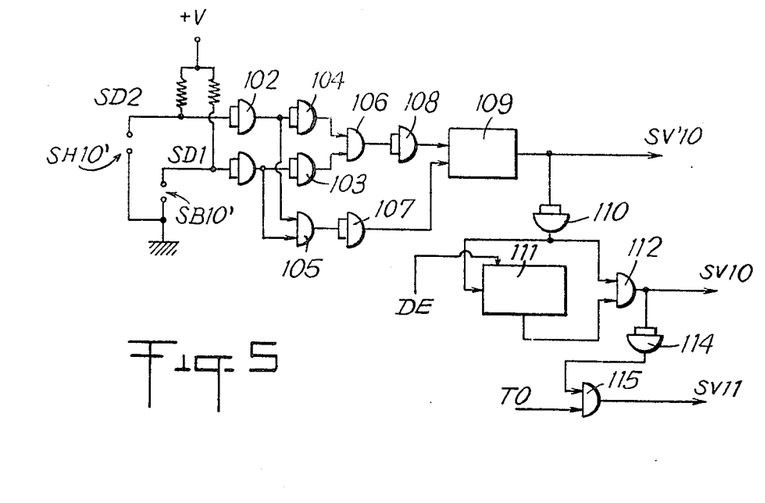
Figure 6:
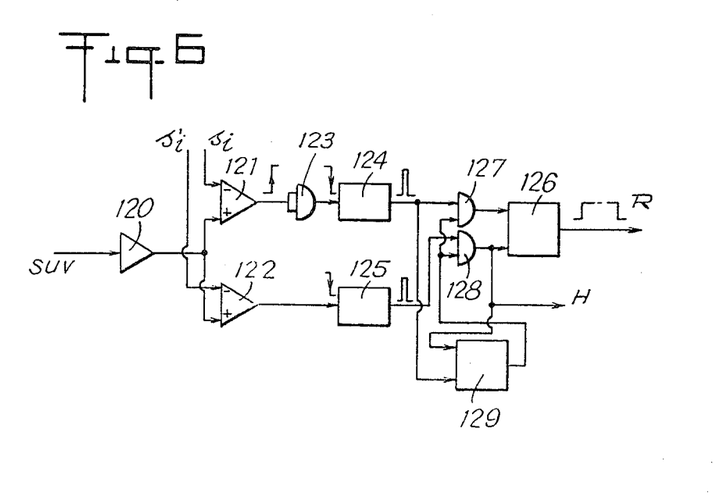

The pulse DE is received by the circuit 35 controlling the sample injection (FIG. 5). Each one of probes SB10', SH10' comprises a pair of spaced apart contacts. One of these contacts is earthed whereas the other is connected to a potential +V, via a high impedance resistor, and to a reversing gate 101, 102 respectively. Signals SD1, SD2 of probes SB10', SH10' are reversed by reversing gates 101, 102 whose output passes to the high logic level when the probes are wet. Output signals from gates 101, 102 are applied, on the one hand, to two reversing gates 103, 104 respectively and, on the other hand, to the two inputs of an AND-type gate 105. Moreover, the outputs of gates 103, 104 are connected to the two inputs of an AND-type gate 106. The output of gate 105 is at the high logic level when the two probes SB10' and SH10' are wet. The output of gate 106 on the contrary is at the high logic level when probes SB10' and SH10' are dry. The output signals from gates 105 and 106 are reversed by reversing gates 107, 108 to control respectively the release and resetting of a flip-flop 109. The signal outputted from flip-flop 109 constitutes control signal SV10'. Said signal is reversed by a gate 110 and applied to the clock input of a one stage binary counter 111. One output of said counter is connected to one input of an AND-type gate 112 whose other input is connected to the output of gate 110. The output signal from gate 112 constitutes control signal SV10. Moreover, the output of gate 112 is also connected to a reversing gate 114 whose output signal is applied to an AND-type gate 115. Said gate 115 receives on another input a signal TO issued from switching circuit 37. Finally, the signal DE is applied to the resetting input of counter 111.

Circuit 35 works as follows The two probes SB10' and SV10' being dry, the output of flip-flop 109 is on the high level, this causing the appearance of signal SV10' which opens electrovalve V10'. The product to be fractionated flows by gravity into the measuring container 10'. When the two probes SB10' and SV10' are wet, the flip-flop 109 changes condition. Signal SV10' stops and the output of gate 110 passes to the high level. The counter 111 is incremented by one unit. A low logic level signal is present on the output of the counter connected to gate 112. Upon the appearance of signal DE, said counter 111 is reset and a high logic level signal appears on its output. The output of gate 112 then passes to the high level, this causing the appearance of signal SV10. The product flows from the measuring container 10'. As soon as the two probes SB10' and SH10' are dry again, the flip-flop 109 changes condition and signal SV10 stops; valve V10 closes but valve V10' on the contrary opens, this permitting to refill the measuring container 10'. Another quantity of product to be fractionated will only be injected in response to another balance detection signal DE. Gate 114 reverses signal V10 and thus allows the passage of signal T0 through the gate 115 to constitute the signal SV11 which commands the opening of the valve V11. Thus, the first eluent contained in container 11 is free to flow into the column before the injection of a quantity of product to be fractionated (balancing of the column with the first eluent), and after that injection (first fraction collection phase).

The circuit 36 controlling the collection of fractions (FIG. 6) receives the measuring signal SUV transmitted by U.V. detector 19a. This signal is amplified by an amplifier 120 and compared to two thresholds $s_i$, $s'_i$ by means of two comparators 121, 122. Thresholds $s_i$ and $s'_i$ are the threshold values which signal SUV must cross in one direction (for $s_i$) in order to control the collection of one fraction, and then in the other direction (for $s'_i$) to stop said collection. Values $s_i$ and $s'_i$ can be adjusted independently one from the other for the different fractions to be collected. The signals representing the preset values of $s_i$ and $s'_i$ which correspond to the fraction whose collection is about to be controlled are produced by switching circuit 37. A reversing gate 123 is connected to the output of comparator 121 to release a monostable circuit 124 when the threshold $s_i$ is crossed in the ascending direction, whereas the output of comparator 122 is directly connected to a monostable 125 to release the latter when the threshold $s'_i$ is crossed in the descending direction. The pulses produced by monostables 124, 125 are applied through AND-type gates 127, 128 to the releasing and resetting inputs of a flip-flop 126 outputting a signal R which controls the collection during the interval between the time when threshold $s_i$ is crossed ascending-wise, and the time when threshold $s'_i$ is crossed descendingwise. A flip-flop 129 receives on its inputs the pulses produced by the monostables 124, 125, respectively directly and after passage through the gate 128, and delivers on its output a signal controlling the gates 127, 128. Flip-flop 129 is released in response to the pulse of monostable 124 and opens gates 127 and 128, and it is reset in response to the pulse of monostable 125, to close gates 127, 128. The signal R, as well as output signal H of gate 128 are transmitted to the switching circuit 37 described hereinafter.

Circuit 37 (FIGS. 3 and 7) is connected to potentiometers PS1 to PS6 and PS'1 to PS'6 delivering signals $s_1$ to $s_6$ and $s'_1$ to $s'_6$ which represent the threshold values of start-of-collection and end-of-collection for the different fractions (in the case of one cycle of chromatography with six eluents). Signal $s_i$ is delivered on an output terminal 130 connected to potentimeters PS1 to PS6 via analog-type respective controlled switches IS1 to IS6, whereas signal $s'_i$ is delivered on an output terminal 131 connected to potentiometers PS'1 to PS'6 via respective controlled switches IS'1 to IS'6. A counter 132 receives signal H on its clock input and comprises a plurality of outputs which are energized successively every time the counter is incremented and which deliver signals T0 and SV12 to SV16. Signals T0 and SV12 to SV16 control respectively the closure of switches (IS1-TS'1) to (IS6-IS'6), and respectively, the closure of controlled analog-type switches IR1 to IR6. Switches IR1 to IR6 receive signal R and deliver signals SV21 to SV26 respectively. These different signals are applied via respective resistors to the base of a transistor 133 connected as a common transmitter and of which the collector, on the one hand, is connected via a resistor 134 to a terminal of potential +V and on the other hand, delivers the signal SV20.

Figure 7:
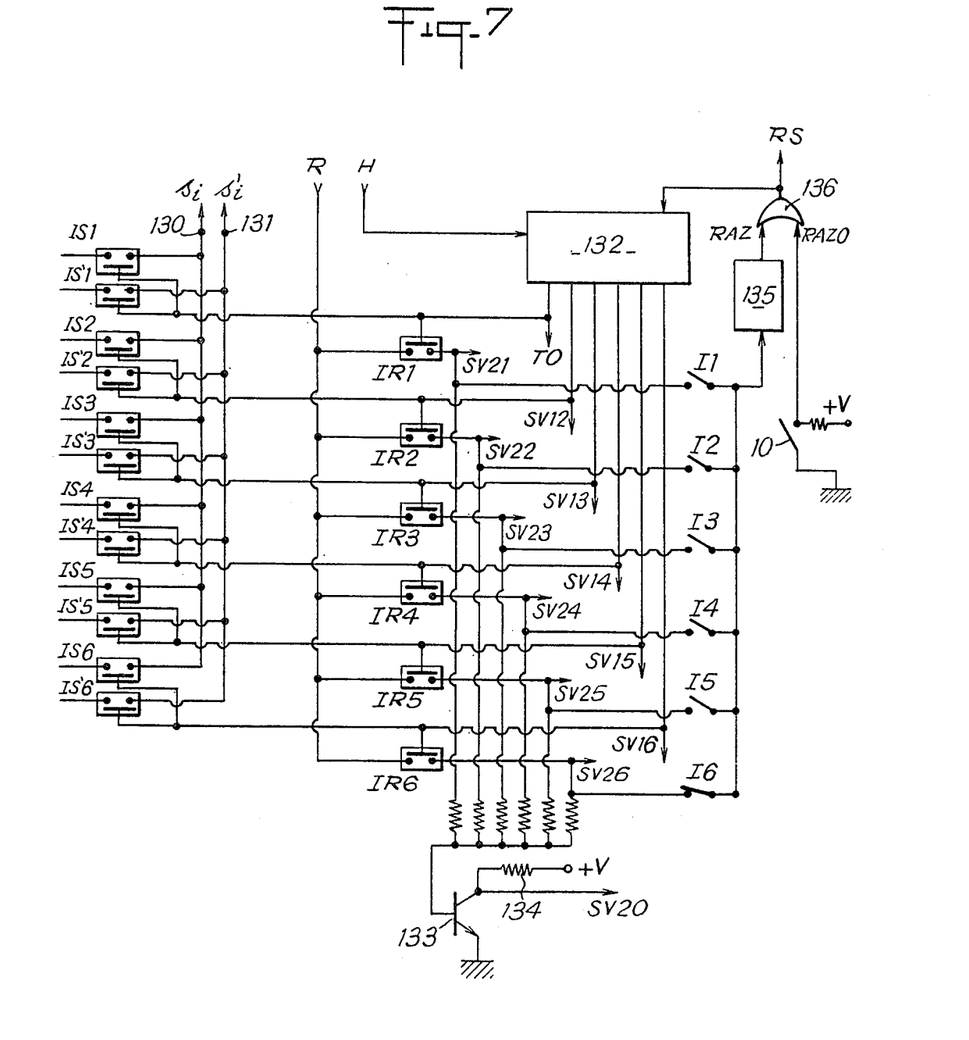

The switching circuit works as follows. At the end of the collection of a fraction corresponding to the eluent of order n (n being between 1 and 5), a pulse H is produced, which increments counter 132 by one unit. A new output of this counter is energized which output controls the closure of the switches of order n+1 with a view to collecting the next fraction. During the intervals between two pulses R, transistor 133 is blocked since there is no high logic level signal on its base. The collector of said transistor is therefore at the high level and the signal SV20 is present. Thus, valve V20 is open and container 20 collects the liquid containing the useless constituents of the product to be fractionated. It will be noted that, immediately after the collection of a fraction, the flip-flop 129 of circuit 36 prevents the transmission of an interfering signal H, such as could be produced if the new threshold $s'_i$, set at the end of the collection, is below the preceding one. Gates 127 and 128 are only re-opened once the new threshold $s_i$ has been crossed. When the fraction corresponding to the last eluent has been collected, the counter 132 is returned to its initial setting and the signal T0 is issued, which signal authorizes the admission of the first eluent for another column-balancing operation.

The return of counter 132 to its initial setting is normally controlled by a reset pulse RAZ produced by a monostable 135. Hand-operated mutually cutting-off switches I1 to I6 receive signals SV21 to SV26 on their first terminals and have their second terminals connected jointly to the input releasing the monostable 135. If the switch I6 is closed, switches I1 to I5 being opened, the back edge of signal SV26 (end of collection of sixth fraction) releases the monostable 135 which, in turn, returns counter 132 to the initial state. In the case where the number of eluents used and of fractions to be collected differs from six, the operator only needs to close that of switches I1 to I6 which correspond to said number. Thus, the end of a cycle of chromatography (re-balancing of the column) is automatically controlled after the collection of the last fraction. The re-initialization of the counter 132 can also be controlled by closing a switch I0 to apply a signal RAZ0 to the re-setting input of counter 132, the switch I0 and monostable 135 being connected to said input via an OR-type gate 136. The manual reset signal RAZ0 can also be transmitted to circuit 35 (FIG. 5) to reset the counter 111. The signal outputted from gate 136 also forms the signal RS applied to the flip-flop 95 of circuit 34 (FIG. 4).

Figure 8:
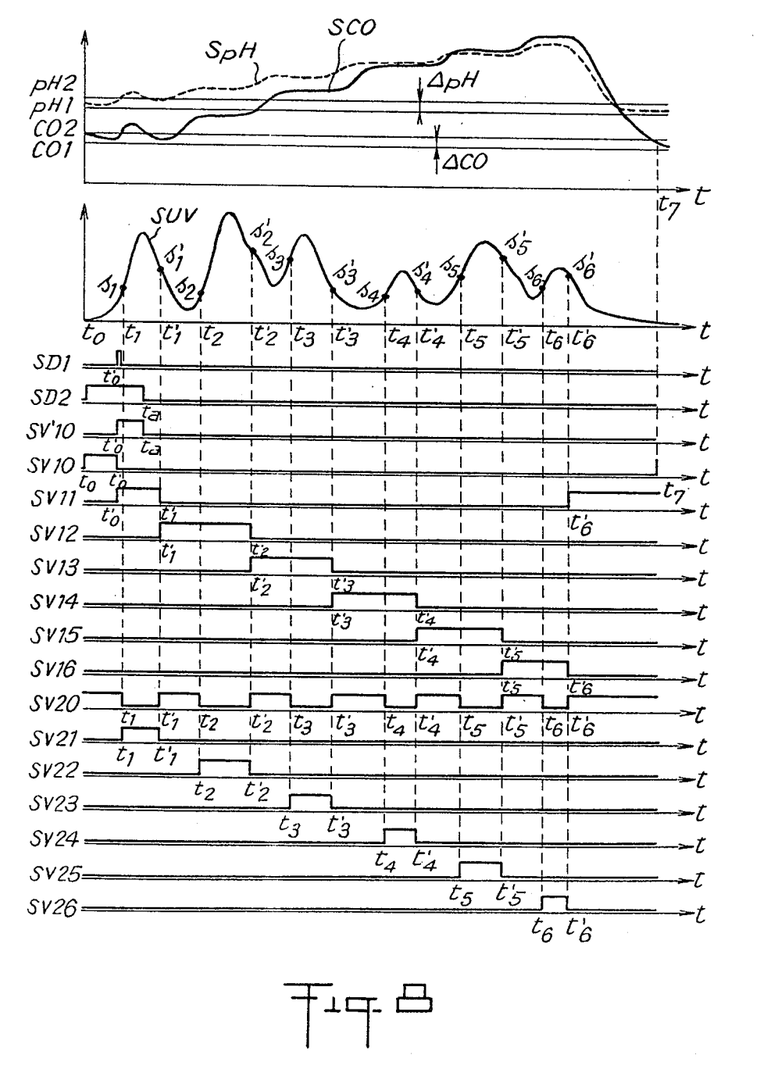
FIG. 8 is a diagram of the signals received and issued by the control unit in the case of a six-stage chromatography.

FIG. 8 illustrates how a sixstage cycle of chromatography is performed.

Arbitrarily, the start of the cycle is selected at moment $t_0$ where the balance-detection signal is produced, i.e. when the measured pH is within the range (pH1, pH2) and when the concentration is within the range (CO1, CO2) (see the curves representing SpH and SCO). At moment $t_0$, electrovalve V10 is open to inject a quantity of product to be fractionated, electrovalves V'10, V11 to V16 and V21 to V26 being in closed position and electrovalve V20 being in open position Soon after $t_0$, the probe SH10' becomes dry and signal SD2 passes to the high level.

At moment $t'_0$, the probe SB10' becomes dry, signal SD1 passes to the high level this causing the closure of electrovalve V10 (end of injection of product to be fractionated) and the opening of electrovalves V'10

(filling of measuring container) and V11 (admission of first eluent). When at moment $t_a$ the two probes SB10' and SH10' are wet, electrovalve V'10 is closed.

The switches IS1, IS'1 and IR1 being closed, the collection of the first fraction starts at moment $t_1$ when the threshold $s_1$ is crossed upwardly (see SUV representative curve) Electrovalve V21 is open whereas electrovalve V20 is closed. At moment $t'_1$, the threshold $s'_1$ is crossed downwardly, this causing the closure of electrovalves V11 and V21, the opening of electrovalves V12 and V20 and the closing of switches IS2, IS'2 and IR2, to collect the second fraction.

The cycle thus continues, electrovalves V22 to V26 being open at moments $t_2$ to $t_6$ when thresholds $s_2$ to $s_6$ are crossed, and closed at moments $t'_2$ to $t'_6$ when thresholds $s'_2$ to $s'_6$ are crossed. Electrovalves V12 to V16 are open at moments $t'_1$ to $t'_5$ and closed at moments $t'_2$ to $t'_6$. Electrovalve V20 is open when all the other output electrovalves are closed.

At the end of the collection of the sixth fraction (moment $t'_6$), electrovalve V11 is re-opened for a re-balancing. Another cycle starts at moment $t_7$ when the column is once again balanced with the first eluent.

Figure 9:
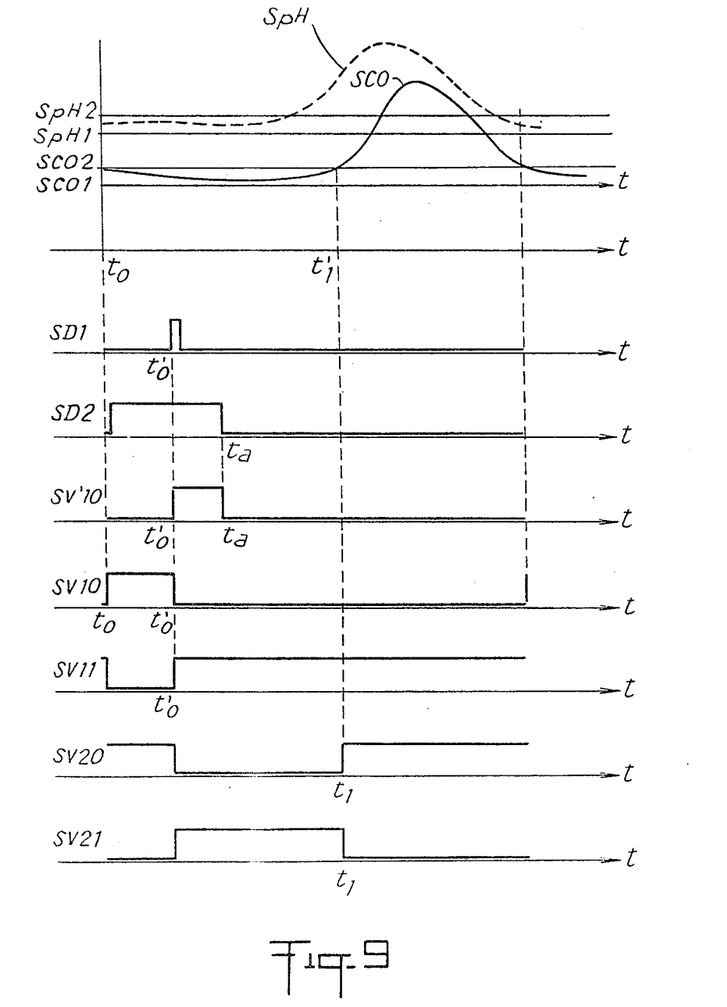
FIG. 9 is a diagram of the signals received and issued by the control unit in the case of a salt-removing operation.

FIG. 9 illustrates another embodiment of the invention in the case of a two-stage chromatography, using two detectors 19b and 19c only. Only one container of eluent 11 and two collector containers 20 and 21 are used.

In this case, the signals SpH and SC0 are used as before, to detect the balance of the column whereas the signal SC0 is also used to control the end of collection of the fraction to be recovered. The start of the collection coincides with the end of the admission of the product to be fractionated. This is true only with the use of certain resins in the column, such as those described in French Patent No. 2 378 808, when the chromatography involved is a salt-removing chromatography, the fraction corresponding to the peak of concentration being in fact the fraction to be rejected. The product to be fractionated having been injected (moment $t'_0$, another re-fill of the measuring container is controlled (moments $t'_0$ to $t_a$) and, also, the opening of electrovalve V11 and of electrovalve V21 and the closure of electrovalve V20.

When at moment $t_1$, the concentration crosses a given threshold (for example threshold SCO2), electrovalve V21 is closed whereas electrovalve V20 is open. The fraction to be recovered is that collected in container 21 whereas the fraction collected in container 20 is that to be disposed of.

Valve V11 being still open, another cycle can start when the column has been re-balanced with eluent.

The installation described hereinabove has the considerable advantage of limiting the work of the operator, for a given chromatography, to presetting the thresholds and to watching the levels inside the containers.

It is known that in many cases, successive chromatographies are necessary to separate a given constituent. To do so, a special control and safety device is provided for each column. And since the fraction recovered in the collector container of a first column is used as product to be fractionated in a second column, said collector container is used in combination with a measuring device as the container of product to be fractionated for the second column.

What we claim is:

1. An automatic installation for liquid chromatography, of the type comprising a chromatographic column, a container of the product to be fractionated, and at least one container of eluent, said containers being connectable with the top of the column via an injection pump, detection means connected to the output of the column and supplying at least one measuring signal representing a characteristic of the liquid discharged from the bottom of the column, means for collecting fractions with at least one collector container which is connectable with the base of the column via an automatically-controlled output valve, and a control unit receiving the measuring signal and comprising means for controlling the fractions collecting means, wherein:
    a level detector is provided for each container of product to be fractionated and of eluent, which detector produces a low level signal whenever the level of the liquid inside the container is below a predetermined threshold,
    automatically controlled feed valves are mounted between the injection pump and each container of product to be fractionated and eluent, respectively,
    a measuring device is provided for the container of the liquid to be fractionated, to allow injection into the column of a pre-determined quantity of said product, and
    the control unit comprises: a control device receiving the or each measuring signal produced by the detection means and controlling on the one hand, the feed and output valves and, on the other hand, the measuring device, to produce successive cycles of chromatography each one including at least the consecutive operations of injecting into the column a set quantity of the product to be fractionated, of admitting in the eluent, and of collecting a fraction; and a safety device connected to the level detectors to control the stoppage of the pump and prevent admission of product to be fractionated or of eluent into the column when the corresponding level detector produces a low-level signal.

2. An installation as claimed in claim 1, wherein the detection device comprises a plurality of detectors producing different measuring signals representing different characteristics of the liquid discharged from the column.

3. An installation as claimed in claim 1, in which the control device is of the type comprising a comparator to initiate the collection of one fraction when a measuring signal produced by the detection means crosses, in one direction, a first preset and adjustable threshold, wherein said control device comprises a second comparator to interrupt the collection of the fraction when the measuring signal crosses in the other direction a second preset threshold adjustable independently of the first.

4. An installation as claimed in claim 1, wherein said control device comprises means of controlling the admission of an eluent into the column and means of detecting the balancing of the column with the admitted eluent, said means responding to at least one measuring signal to control the injection of a quantity of product to be fractionated.

5. An installation as claimed in claim 4, wherein the balance detection means comprise a comparison device receiving said measuring signal and producing an output signal when the amplitude of the measuring signal is within an adjustable predetermined range.

6. An installation as claimed in claim 4, wherein the balance detection means comprise a circuit for eliminating any untimely detection.

7. An installation as claimed in claim 4, wherein said installation comprises a plurality of containers of eluent and the control device receives the measuring signal or signals from the detection device for controlling the successive cycles, each one comprising: the injection of a predetermined quantity of product to be fractionated, the admission of a first eluent into the column, the collection of a first fraction, the admission of a second eluent into the column, the collection of a second fraction, and if necessary, at least one additional sub-cycle comprising the admission of another eluent into the column and the collection of the corresponding fraction, and finally the admission of the first eluent into the column to re-balance it before the start of the next cycle.

8. An installation as claimed in claim 7, wherein the control device comprises means of controlling the admission of eluent acting in response to the end of the injection of the product to be fractionated or to the end of the collection of one fraction.

9. An installation as claimed in claim 1, wherein said installation comprises a plurality of collector containers, each one of which is associated to a single output valve controlled by said control device to connect the container with the column, and to a level detector which is designed to produce a high level signal when the level of the liquid inside the container rises above a predetermined threshold, said detector being connected to the safety device.

10. An installation as claimed in claim 1, wherein the detection means comprise a concentration detector equipped with a tube through which can flow the liquid discharged from the column, a coil wound about said tube, and a measuring circuit to measure the variations of inductance of the coil.

11. An installation as claimed in claim 1, wherein said installation comprises a plurality of chromatographic columns each one with its own control unit, and a collector container associated to one column is combined with measuring means to constitute the container of product to be fractionated feeding another column.

12. An installation as claimed in claim 1, wherein said measuring means consist of a container provided with two probes placed at different levels, which container is connectable, on the one hand, with the container of product to be fractionated via a first valve, and on the other hand, with the column via a second valve, and the control device comprises a circuit receiving the signals of the two level probes associated to the measuring device and a control signal, said control device controlling the valves in order to introduced into the measuring container or extract therefrom a quantity of liquid corresponding to the level differences between the two probes.

* * * * *